United States Patent
Weiss

(10) Patent No.: US 7,450,983 B2
(45) Date of Patent: Nov. 11, 2008

(54) AUTOMATED BRAIN MRI AND CT PRESCRIPTIONS IN TALAIRACH SPACE

(75) Inventor: Kenneth L. Weiss, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 466 days.

(21) Appl. No.: 10/803,700

(22) Filed: Mar. 18, 2004

(65) Prior Publication Data

US 2005/0165294 A1 Jul. 28, 2005

Related U.S. Application Data

(60) Provisional application No. 60/455,969, filed on Mar. 18, 2003.

(51) Int. Cl.
*A61B 5/05* (2006.01)
(52) U.S. Cl. .............. 600/410; 600/414; 600/417; 600/422; 382/128; 128/922
(58) Field of Classification Search ......... 600/410–417, 600/425; 606/130; 128/922; 382/128; 324/307–309
See application file for complete search history.

(56) References Cited

U.S. PATENT DOCUMENTS

| | | | | |
|---|---|---|---|---|
| 4,706,665 | A | * | 11/1987 | Gouda ............ 606/130 |
| 5,546,472 | A | * | 8/1996 | Levin ............ 382/131 |
| 5,632,276 | A | * | 5/1997 | Eidelberg et al. ......... 600/414 |
| 6,195,409 | B1 | | 2/2001 | Chang |
| 6,560,354 | B1 | | 5/2003 | Maurer, Jr. |
| 6,574,304 | B1 | | 6/2003 | Hsieh et al. |
| 6,608,916 | B1 | | 8/2003 | Wei et al. |
| 6,937,750 | B2 | | 8/2005 | Natanzon |
| 6,950,542 | B2 | | 9/2005 | Roesch |
| 6,952,097 | B2 | | 10/2005 | Schreck |
| 6,996,261 | B2 | * | 2/2006 | deCharms ............ 382/131 |

(Continued)

OTHER PUBLICATIONS

Ardenkani, Babak A.; Kershaw, Jeff;Braun, Michael; Kanno, Iwao, Automatic Detection of the Mid-Sagittal Plane in 3-D Brain Images, IEE Transactions on Medical Imaging, vol. 16, No. 6, Dec. 1997, pp. 947-952.

(Continued)

*Primary Examiner*—Brian L. Casler
*Assistant Examiner*—Amanda L. Lauritzen
(74) *Attorney, Agent, or Firm*—William S. Morriss; Frost Brown Todd LLC

(57) ABSTRACT

Brain Magnetic Resonance Imaging (MRI), Computerized Tomography (CT), or other diagnostic modalities may employ a three-step procedure during initial ("scout") cranial pre-scans that corrects for patient positioning (i.e., roll, yaw and pitch) to reduce inter- and intra-patient variation, thereby enhancing the diagnostic and comparative value of subsequent detail scans even across different diagnostic platforms. In MRI, for instance, locating the saggital sinus (SS) and optimizing a line to bisect the brain through this SS may be automated to correct for roll and yaw. By then identifying the contour of the corpus callosum in a lateral saggital scout scan, the Talairach anterior commissure (AC)—posterior commissure (PC) reference line may be found for correcting pitch. Prescription of detailed scans are improved, especially when the three-step correction is repeated periodically identifying the need to repeat a detailed scan or to adjust the coordinates of a subsequent scan.

12 Claims, 12 Drawing Sheets

U.S. PATENT DOCUMENTS

| | | | |
|---|---|---|---|
| 7,110,587 | B1 | 9/2006 | Natanzon |
| 2002/0143575 | A1 | 10/2002 | Hansen et al. |
| 2003/0095692 | A1 | 5/2003 | Mundy et al. |
| 2005/0070781 | A1* | 3/2005 | Dawant et al. ............. 600/407 |
| 2006/0025673 | A1 | 2/2006 | De Leon |
| 2006/0036152 | A1* | 2/2006 | Kozel ......................... 600/410 |
| 2006/0173274 | A1* | 8/2006 | George et al. ............... 600/409 |
| 2006/0233430 | A1* | 10/2006 | Kimura ...................... 382/128 |

OTHER PUBLICATIONS

Vérard, Laurent; Allain, Pascal; Travére, Jean Marcel; Baron, Jean Claude; Bloyet, Daniel, Fully Automatic Identification of AC and PC Landmarks on Brain MRI Using Scene Analysis, IEEE Transactions on Medical Imaging, vol. 16, No. 5, Oct. 1997, pp. 610-616.

Woods, Roger; Dapretto, Mirella; Sicotte, Nancy L.; Toga, Arthur W.; Mazziotta, John C., Creation and Use of a Talairach-Compatible Atlas for Accurate, Automated, Nonlinear, Intersubject Registration, and Analysis of Functional Imaging Data, Human Brain Mapping, vol. 8, 1999, pp. 74-79.

Itti, Laurent et al., Automatic Scan Prescription for Brain MRI, Magnetic Resonance in Medicine 45 (2001) pp. 486-494.

Flecken, P.; Tranum-Jensen, J., Principles and Techniques of Nomenclature and Positioning, In: Anatomy in Diagnostic Imaging, 2nd ed., Philadelphia: WB Saunders; 2001.

Woodburne, Russell T., A.M., Ph. D., Prof of Anatomy at Univ. of Michigan Medical School, Essentials of Human Anatomy, 5th ed., New York, Oxford Univ. Press, 1973.

* cited by examiner

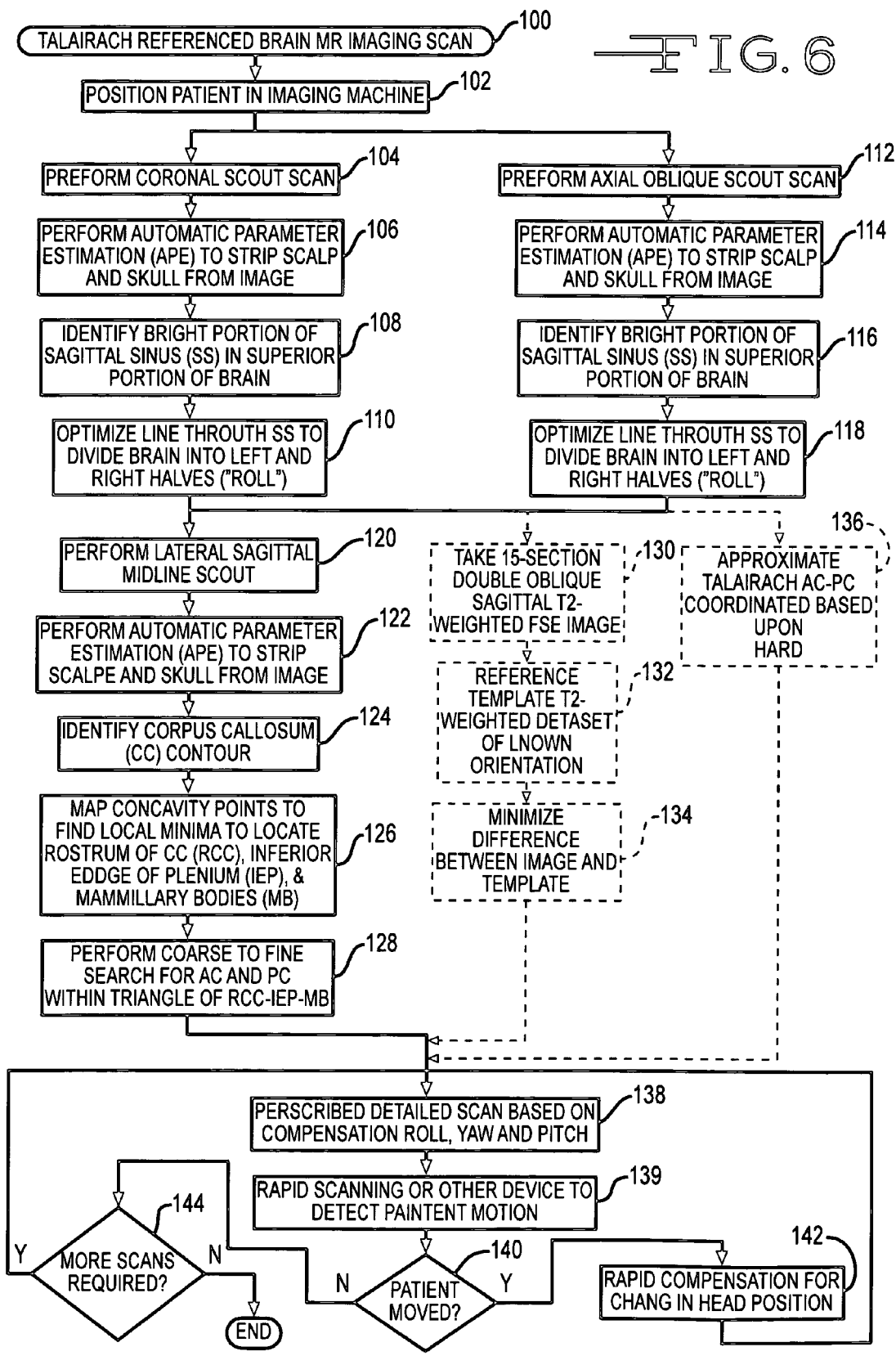

AUTOMATED BRAIN MRI AND CT PRESCRIPTIONS IN TALAIRACH SPACE

CROSS REFERENCE TO RELATED APPLICATIONS

The present application hereby claims the benefit of the provisional patent application entitled "CLINICAL BRAIN MRI PRESCRIPTIONS IN TALAIRACH SPACE", Ser. No. 60/455,969, filed on 18 Mar. 2003.

FIELD OF THE INVENTION

The present invention relates, in general, to devices that utilize a diagnostic imaging modality (e.g., magnetic resonance imaging (MRI) or x-ray-based Computerized Tomography (CT)), and more particularly to an automated system and method for interpreting a diagnostic screening scan to spatially orient to minimize inter- and intra-patient variability and to autoprescribe regions for a subsequent detailed scan.

BACKGROUND OF THE INVENTION

Medical diagnostic imaging is increasingly relied upon to detect various physical maladies. For example, X-ray-based Computerized Tomography (CT) is particularly suited for detection of skeletal injuries and dense cancerous lesions. As another example, Magnetic Resonance Imaging (MRI) is particularly well suited for detecting soft tissue conditions such as strokes, aneurysms and arterial blockages.

While advances in MRI and CT diagnostic systems have reduced the amount of time necessary, clinical diagnostic imaging still requires a significant amount of time to perform a detailed scan of a region of interest of a patient. Once the detailed scan is obtained, an expert clinician must interpret the results, often challenged by inter-patient and intra-patient scan variations. In particular, the expert clinician seeks to recognize anatomical landmarks and to identify departures from a normal tissue structure by having the scan spatially oriented and normalized for an easier comparison to a previously taken scan for the same patient or perhaps to other patients. It would be further desirable that such orientation would be normalized even between different imaging modalities (e.g., MRI, CT) so these results may assist in future diagnostic procedures for the patient.

Consequently, a significant need exists for an automated approach to performing cranial scout scans that identify roll, yaw and pitch in order that corrections relative to a standard may be accomplished so that useful comparisons may be made with other head scans for the same patient or other patients.

SUMMARY OF THE INVENTION

The invention overcomes the above-noted and other deficiencies of the prior art by providing an automated procedure that corrects for patient's head not being aligned by performing image analysis of a diagnostic image to determine coordinates of a Talairach anterior commissure (AC)—posterior commissure (PC) reference line. Thereby, subsequently prescribed scans are oriented, minimizing intra- and inter-patient positioning variability. Thus, further diagnostic and therapeutic measures may be employed that benefit from having known relative coordinates from scan to scan.

In one aspect of the invention, a method, medical diagnostic system, and computer product provide for identifying a head position of a patient undergoing diagnostic imaging by obtaining a diagnostic image of a patient's head. Image processing determines coordinates of the Talairach AC-PC reference line within the diagnostic image and defines a coordinate system of the diagnostic image with reference to the Talairach AC-PC reference line. Thereby, prescriptions for detailed scans and for checking for needed position corrections are enhanced.

These and other objects and advantages of the present invention shall be made apparent from the accompanying drawings and the description thereof.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5A is an image of APE to determine the positions of the scalp and CC by examining intensities along the central column of pixels from a midline sagittal T2-weighted image. FIG. 5B is an image of automated contours and a bisecting line on a 2-second axial oblique T1-weighted gradient-recalled echo image. FIG. 5C is an image of outline of the CC, triangle search mask, and Talairach AC-PC reference line on a midline sagittal T2-weighted image.

FIG. 6 is a flow diagram or sequence of operations for performing a three-step roll, yaw and pitch correction for an MR imaging prescan.

DETAILED DESCRIPTION OF THE INVENTION

BACKGROUND AND PURPOSE: Variability in patient head positioning may yield substantial inter-study image variance in the clinical setting. We describe and test three-step technologist and computer-automated algorithms designed to image the brain in a standard reference system and reduce variance.

METHODS: Triple oblique axial images obtained parallel to the Talairach anterior commissure (AC)-posterior commissure (PC) plane were reviewed in a prospective analysis of 126 consecutive patients. Requisite roll, yaw, and pitch correction, as three authors determined independently and subsequently by consensus, were compared with the technologists' actual graphical prescriptions and those generated by a novel computer automated three-step (CATS) program. Automated pitch determinations generated with Statistical Parametric Mapping '99 (SPM'99) were also compared.

RESULTS: Requisite pitch correction (15.2°±10.2°) far exceeded that for roll (−0.6°±3.7°) and yaw (−0.9°±4.7°) in terms of magnitude and variance (P<0.001). Technologist and computer-generated prescriptions substantially reduced inter-patient image variance with regard to roll (3.4° and 3.9° vs. 13.5°), yaw (0.6° and 2.5° vs. 22.3°), and pitch (28.6°, 18.5° with CATS, and 59.3° with SPM'99 vs. 104°). CATS performed worse than the technologists in yaw prescription, and it was equivalent in roll and pitch prescriptions. Talairach prescriptions better approximated standard CT canthomeatal angulations (9° vs. 24°) and provided more efficient brain coverage than that of routine axial imaging.

Although the Talairach anterior commissure (AC) posterior commissure (PC) reference standard has been widely embraced by the neuroscience community, routine clinical brain MR imaging is still typically performed in the standard three orthogonal planes of the magnet with little regard to patient positioning. This approach makes inter-pretation and intra-patient or inter-patient comparisons more difficult. Advances in MR imaging hardware and software have made patient-optimized oblique imaging in a standard reference frame more feasible and more readily implemented than when it was originally reported.

Figure 1:
FIG. 1 depicts a coned-done midline sagittal FSE T2-weighted MR image of a human brain,Talairach and Schaltenbrand anterior commissure ("AC")—posterior commissure ("PC") reference lines and corpus callosum ("CC") annotated thereon.

Talairach and co-workers defined their inter-commissural basal brain line as passing through the superior edge of the AC and the inferior edge of the PC (FIG. 1). The stereotactic atlas of Talairach and Tournoux, based on the brain of a 60-year-old right-handed French woman, has become the de facto standard reference almost universally used in functional brain imaging. Researchers often transform their structural and functional data into Talairach space, which serves as a common coordinate reference system.

The AC is composed of fiber bundles involved in interhemispheric transfer of temporal and orbitofrontal cortex axons. In the midline, the AC is immediately in front of the anterior columns of the fornix and inferoposterior to the rostrum of the corpus callosum (CC). The PC consists of a variety of cell groups located anterior to the pineal region. It is posterior to central gray matter and rostral to the superior colliculi at the junction of the third ventricle and aqueduct of Sylvius. Pupillary light reaction and vertical eye movement is believed to be mediated by the PC.

As a slight modification of the Talairach reference, Schaltenbrand and others have chosen the line connecting the middle of the AC and PC. An axial section passing through the Schaltenbrand reference line should depict both commissures simultaneously, whereas with the Talairach reference, the commissures are separately visualized on adjacent thin sections. Although perhaps more compelling from an MR imaging perspective, the Schaltenbrand line has not gained dominance over the more established Talairach reference.

In FIG. 1, a midline sagittal FSE T2-weighted MR image is depicted of a human skull (TRITE, 3816/105eff; echo train length, 16; section thickness, 4 mm; matrix, 512×256; FOV, 20 cm) with a solid line and dotted line correspond to the Talairach and Schaltenbrand AC-PC reference lines.

The CC has also been proposed as a reference system, as it may be appreciated, even with low resolution MR imaging, angiography, and positron emission tomography. However, partly because of its relatively inconstant relationship to central gray matter nuclei, the CC has not achieved the status of the AC-PC line as a universal basal reference.

It has been previously proposed to automated image prescriptions based on surface mapping to a standard template brain. This method, however, requires the acquisition of a nonclinical brain series and relies on surface features that may he variable and that may have an even more inconstant relationship to central gray matter nuclei than the CC. Moreover, such an algorithm lacks a technologist-driven correlate that might permit more widespread adoption of their proposed reference standard.

To perform direct Talairach-referenced MR imaging examinations, we recently introduced a rapid three-step protocol. This consecutively corrected roll (y-rotation, i.e., rotation about an axis along the anteroposterior direction), yaw (z-rotation, i.e., rotation about an axis along the superoinferior direction), and pitch (x-rotation, i.e., rotation about an axis along the left-right direction). To improve conspicuity of the AC and PC and to provide diagnostic coverage of the brain in the sagittal projection, we substituted a 15-section fast spin-echo (FSE) T2-weighted sequence for their single-shot FSE (SSFSE) imaging protocol and established this as our routine clinical protocol in October 2001.

Our prospective study was designed to test the efficacy of our revised protocol in the clinical setting and assess the potential for computer automation. We hypothesized that the protocol leads to a reduction in inter-subject image variance, that it better approximates the canthomeatal CT reference line, and that it provides more efficient brain coverage than standard axial imaging. Additionally, we hypothesized that each step of the protocol could be successfully automated.

Methods—Patient Selection. Institutional review board approval was obtained. We prospectively examined 126 consecutive patients (64 male, 62 female) who underwent imaging at our institution with the three-step clinical AC-PC protocol in a 2-week period from May 7, 2002, to May 21, 2002. The mean age of our subject population was 49.2 years ±17.8 with a range of 17-89 years.

Figure 2A:
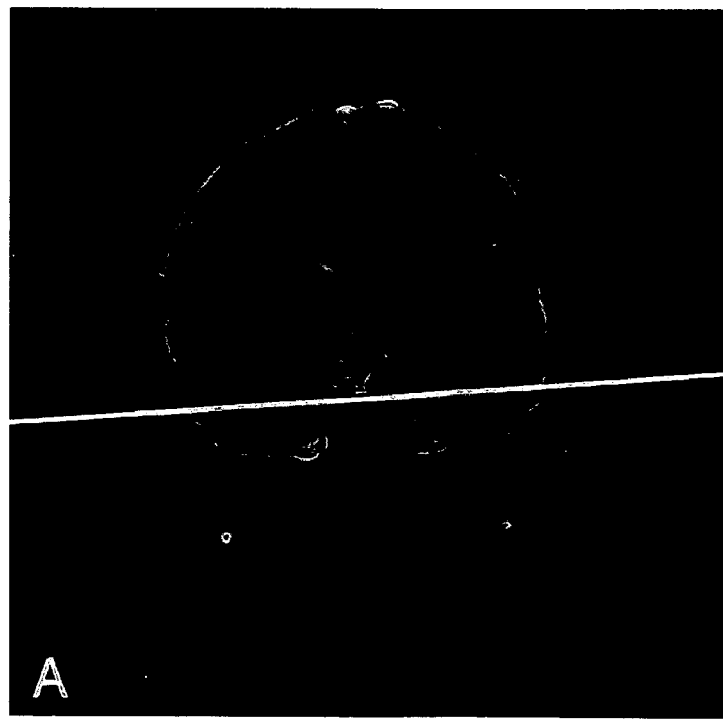
FIGS. 2A-2C are sequential images from a single patient's three-step clinical AC-PC protocol, with FIG. 2A depicting a coronal FGRE localizer image, FIG. 2B depicting a roll-corrected axial oblique FGRE localizer image, and FIG. 2C depicting a roll- and yaw-corrected double oblique T2-weighted FSE image.
Figure 2B:
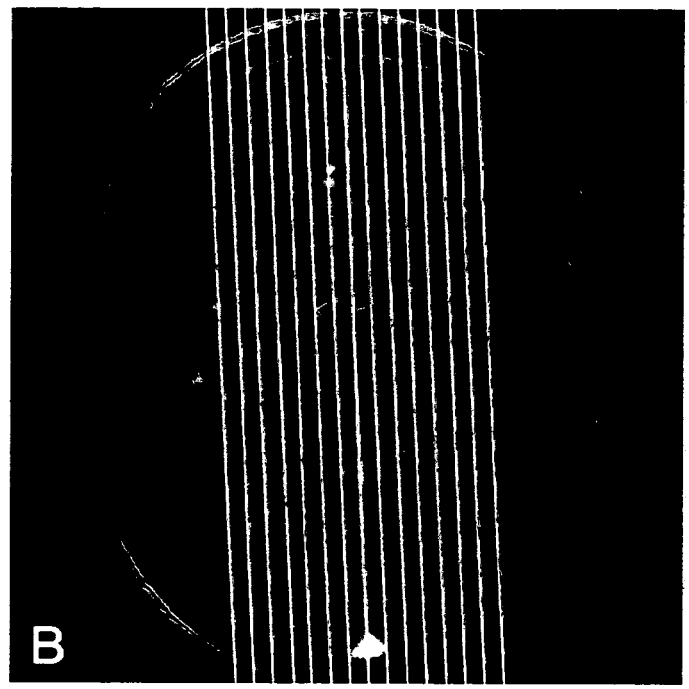
Figure 2C:
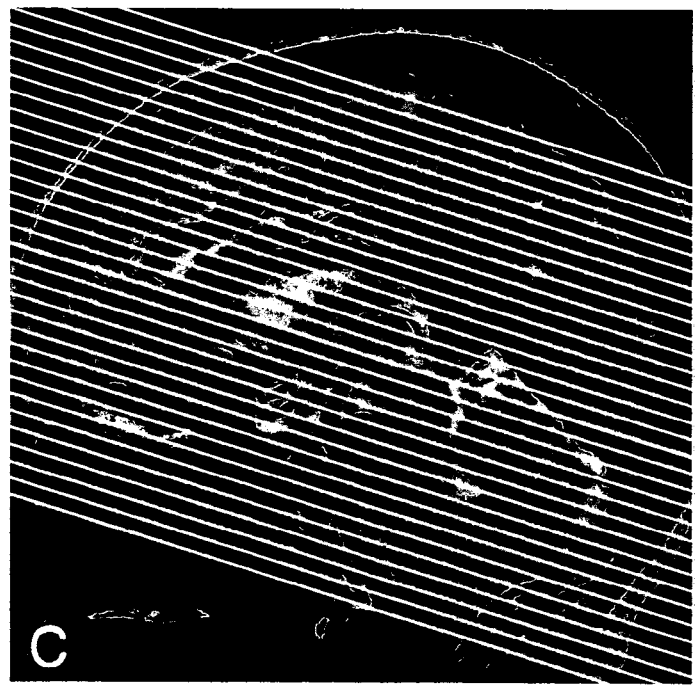

Imaging Protocol. All MR imaging studies were performed with one of two 1.5-T whole-body units (GE Medical Systems, Milwaukee, Wis.) at our institution. Patients were secured in the standard head coil after alignment was optimized by means of visual inspection. In the clinical protocol tested, a three-step technique sequentially corrected for patient roll, yaw, and pitch. First, a 2-second fast gradient-recalled echo (FGRE) coronal scout image was obtained, from which a similar 2-second axial oblique FGRE image was prescribed, with a correction for patient roll (FIG. 2A). Subsequently, 15 double oblique sagittal T2 FSE sections were prescribed from this axial oblique image, with corrections for roll and yaw (FIG. 2B). Finally, axial triple oblique images were prescribed from the adjusted midline sagittal image parallel to the AC-PC line, as described by Talairach (FIG. 2C). Identical 4-mm, interleaved sections are typically obtained for all axial oblique sequences, simplifying setup and allowing for advanced prescription. Coronal sequencing perpendicular to the AC-PC line may also be prescribed in advance from the sagittal double oblique sequence or subsequently from the triple oblique axial series.

Criterion Standard Determination. To establish a criterion standard, independent blinded measurements of required roll, yaw and pitch correction were made by three co-authors (J. L. W., W. S., K. L. W., the last a board certified radiologist with a Certificate of Added Qualification in neuroradiology) by using custom designed software. Corrections in a clockwise direction were assigned positive values, and counterclockwise corrections were assigned negative values.

For roll and yaw determination, the three co-author measurements were averaged and 15% of cases (19 of 126 cases) with greatest co-author variance were reexamined. These cases were independently reexamined by each co-author, and a 20% trimmed mean was computed to reduce the influence of outliers by discarding both the largest and the smallest measurement and by averaging the four remaining values for each discordant case.

For pitch, the custom software recorded x- and y-coordinate selections from the midsagittal image for the superior edge and center of the AC and for the inferior edge and center of the PC. For each image, the greatest distance of any single observation from the mean was used as a score. Each of the three co-authors independently reexamined the 15% of cases (19 of 126) with the highest score, and they also subsequently reviewed these cases as a group to achieve a consensus and to remove outliers.

Canthomeatal Pitch and Requisite Axial Coverage Determinations. To assess canthomeatal pitch relative to the Talairach AC-PC line, we retrospectively reviewed surface-rendered three-dimensional (3D) datasets from both the archetypical single individual Montreal Neurologic Institute (MNI) brain (14) and the averaged MNI brain (15), the latter obtained from 305 healthy volunteers. The angle subtended by a line drawn through the orbital canthus and external acoustic meatus and a line drawn through the superior edge AC and inferior edge PC were measured, as in FIG. 3.

Figure 4:
FIG. 4 is an image of requisite brain volume coverage: Talairach versus average axial sectioning for the archetypical MNI brain (14). Solid lines are Talairach referenced. Dotted lines correspond to an average patient head position oriented 15.1' counterclockwise from AC-PC. Measurements are in millimeters. Note the reduction in brain volume coverage afforded by Talairach obliquity compared with standard axial imaging.

To assess requisite axial brain coverage, the distance from the foramen magnum (tonsillar tip) to the brain convexity was measured twice, once perpendicular to the Talairach AC-PC line and once perpendicular to a line representing the mean patient obliquity in our study. Measurements were made on the archetypical MNI brain, as depicted in FIG. 4, the average MNI brain, and an archetypically positioned patient from our study.

Technologist Measurements. A total of 15 technologists imaged patients with the AC-PC protocol during the 2-week study period. Technologists of record had a wide range of MR imaging expertise (ranging from students in training to chief technologists), and experience with the tested protocol varied from 1 day to 8 months. Technologist prescriptions were derived from the orientation information contained within the Digital Imaging and Communications in Medicine (DICOM) headers of the triple oblique clinical scans. These calculations were automated by using DCMTK (Kuratorium OFFIS; Oldenburg, Germany) and Matlab 6.1 (The MathWorks, Inc, Natick. Mass.).

Computer Algorithms. In FIG. 6, computer algorithms or procedure 100 may emulate and substitute for each step of the technologist-driven three-step clinical protocol for the triplanar brain MR imaging scan. These computer automated three-step (CATS) algorithms 100 were implemented in Matlab 6.1 as C-language MEX extensions, and they were developed by using a training dataset of 48 randomly selected clinical brain MR imaging studies from our institution.

It should be appreciated that two-dimensional or three-dimensional diagnostic imaging scans may be performed with roll and yaw corrections performed sequentially or simultaneously with the goal of obtaining a sagittal midline image for processing to locate or approximate the Talairach AC-PC reference line.

Figure 5A:
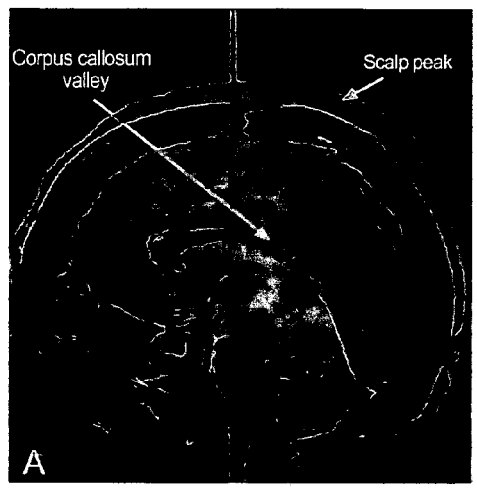
FIGS. 5A-5C are an illustration of computer automated three-step functionality.
Figure 5B:
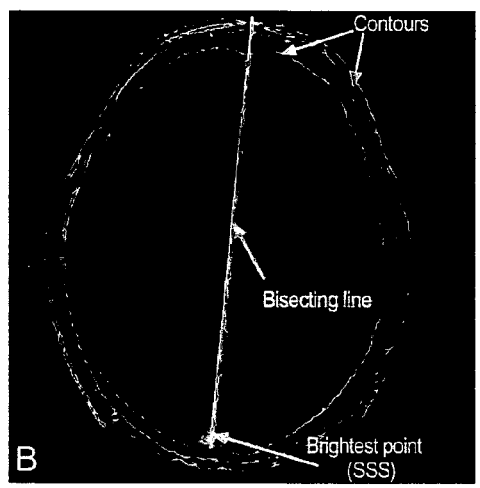

The roll and yaw algorithms used coronal or axial oblique 2-second FGRE images, respectively, to identify the sagittal sinus in cross section and to find lines through the sagittal sinus that bisect the brain. An automatic parameter estimation (APE) method found intensity thresholds for the scalp and skull by examining intensity peaks along the central column of pixels (FIG. 5A). Boundaries for scalp, skull and brain regions of the image were then determined by using the contours based on these intensities, and the scalp and skull were stripped. Next, the algorithm identified the brightest point of the stripped image in a superior portion of the coronal image or in a posterior portion of the axial image. This point was presumably within the sagittal sinus. Roll or yaw was determined by optimizing the slope of a line passing through this point to approximately bisect the area of the brain (FIG. 5B).

With particular reference to FIG. 6, the patient is positioned in the imaging machine (block 102). A coronal scout scan is performed (block 104). APE is performed to strip scalp and skull from the coronal scout image (block 106). The bright portion corresponding to the sagittal sinus (SS) is identified in an upper portion of the image (block 108). By bisecting the area of the brain image with a line that passes through the SS, the roll angle of the brain is determined (block 110).

An axial oblique scout scan is performed orthogonal to the roll axis (block 112). APE is performed to strip the scalp and skull from the image, leaving the image of the brain (block 114). The bright portion corresponding to the SS is located in a posterior portion of the brain image (block 116). Then a line passing through the SS is optimized to bisect the brain image, thus defining the yaw angle of the brain imaging (block 118).

Figure 5C:
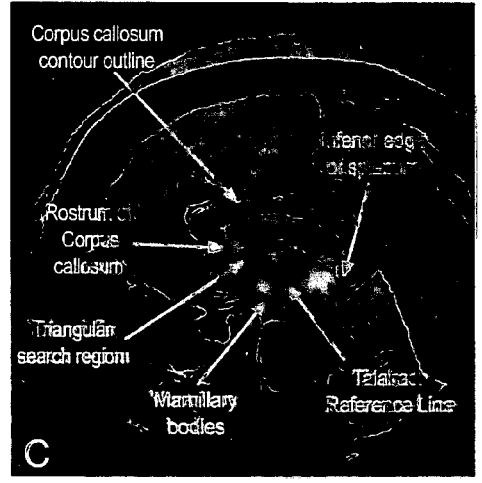

The pitch algorithm automatically determined the positions of the AC and PC from a single midline sagittal T2-weighted image (block 120) and computed both Talairach and Schaltenbrand AC-PC reference lines. For pitch, CC was located by means of APE (FIG. 5A), and its shape was used to predict the locations of the AC and PC. Two imaging features were extracted to locate the CC, AC, and PC: A contour was used to identify the boundary of the CC (FIG. 5C and block 124 of FIG. 6), and a map of concavity points identified local minima (block 126). After the scalp and skull were removed (block 122), contour lines were used to determine the boundary of the CC. Then, the shape of the CC was used to locate the rostrum of corpus callosum (RCC) and the inferior edge of the splenium (IES), as well as to predict the location of the mammillary bodies (MB) by using the concavity map (block 126). The algorithm used a coarse-to-fine strategy to search for the AC and PC (block 128). The area roughly defined by the triangle formed by the RCC, IES, and MB was assumed to contain the AC and PC. Candidate positions for both were statistically estimated from the shape of the CC, and the two nearest concavity points were chosen as the AC and PC (FIG. 5C). If no suitable concavity point was found, the estimate was used. Therefore, as long as the CC was identified, Talairach and Schaltenbrand AC-PC reference lines could be derived.

An alternate computer-based method to determine pitch is to minimize the difference (block 134) between the 15-section double oblique sagittal T2-weighted FSE image obtained (block 130) and a template T2-weighted dataset of known orientation (block 132). SPM'99 (Statistical Parametric Mapping '99; Wellcome Department of Cognitive Neurology, Institute of Neurology, London, England) is a freely available Matlab software package that implements this functionality for MR imaging. The T2-weighted template provided with SPM'99 and used in this study was derived from the MNI average brain (14-16). To facilitate direct comparisons to the pitch algorithm described previously, we assumed that technologists had adequately corrected for roll and yaw and trivially modified SPM'99 to allow affine normalization with rotation only for pitch. Parenthetically, because of the limited brain coverage afforded by the 15 sagittal sections, SPM'99 functioned erratically without this rotational constraint.

As yet a further alternative computer-based method to determine pitch is to locate the patient's hard palate in a lateral midline image and define the Talairach AC-PC reference line as being 12 degrees from this line (block 136), as described in greater detail below with regard to computerized tomography (CT).

After the Talairach AC-PC reference line is defined, subsequent detailed scans may be prescribed with appropriate coordinates and corrections for roll, yaw and pitch (block 138). It should be appreciated that some diagnostic modalities require a significant amount of time to complete detailed scans. In addition, some scanning arrangements do not physically constrain the patient within a specific orientation. Thus, it is advantageous to perform rapid scanning to detect patient motion (block 139). If the patient has moved (block 140), then rapid compensation for change in head position is performed (block 142) and processing returns to block 138. Else, a determination is made as to whether more detailed scans are required using existing correction (block 144). If so, processing returns to block 138.

Statistical Analysis. Statistical analyses were performed in NCSS 2001 (NCSS and PASS; Number Cruncher Statistical Systems, Kaysville, UT, available at www.ncss.com) and Excel (Microsoft, Redmond, Wash.). For each angle prescription, deviation from the criterion standard measures precision, and absolute deviation from the criterion standard was used to measure accuracy. To test whether accuracy in roll determination was influenced by patient yaw, we performed a Pearson correlation coefficient analysis.

Results. Criterion Standard Data Analysis inter-author variance (co-author inter-observer error) was low overall, with only a few measurements requiring review and consensus determination (FIG. 6). Despite efforts to physically align the patients, most individuals demonstrated some degree of head roll and yaw. Mean roll was $-0.6°\pm37°$, and mean yaw was $-0.9°\pm4.7°$ (Table 1).

Figure 7A:
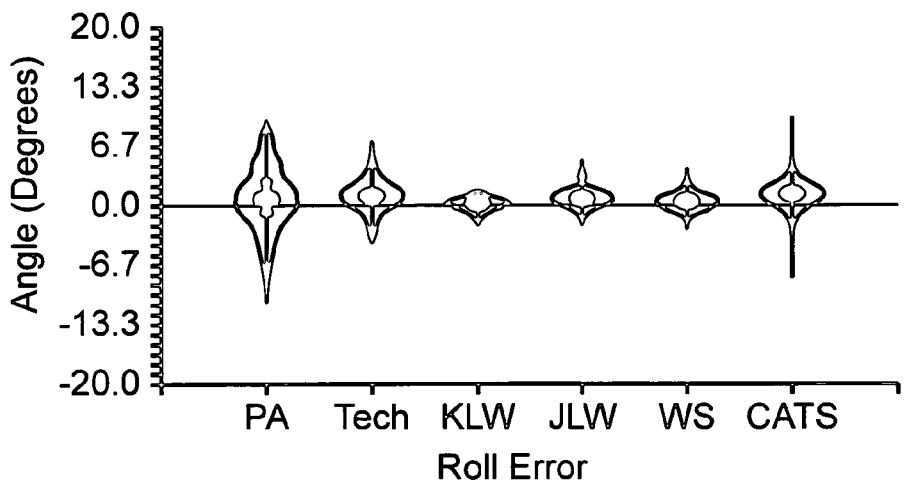
FIGS. 7A-C are violin plots of roll, yaw and pitch prescription errors, comparing technologist (Tech), computer (CATS and SPM'99) methods with physical alignment (PA), wherein spread narrowing indicates reduced image variability.
Figure 7B:
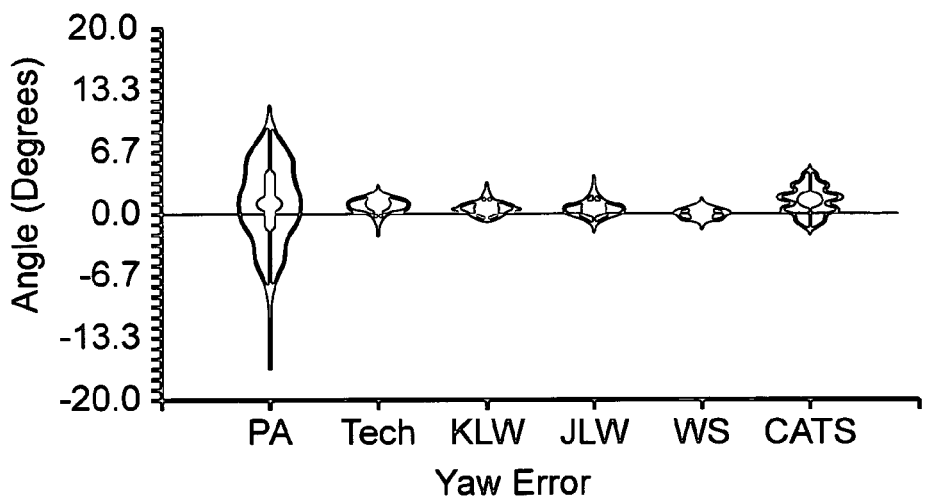
Figure 7C:
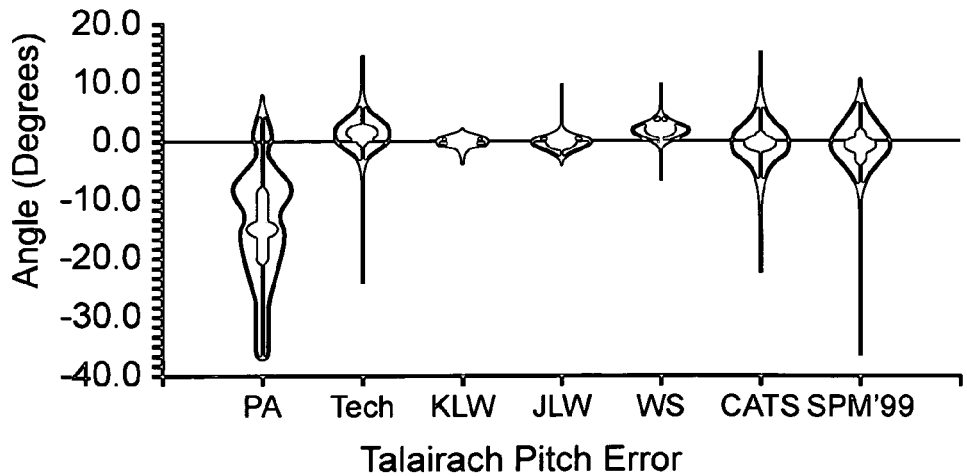

In two pitch determinations, a consensus could not be reached, and a criterion standard was not established, leaving 124 cases for comparison with technologist and computer algorithm prescriptions. Talairach pitch was $15.2°\pm10.20$, and Schaltenbrand pitch was $9.4°\pm10.4°$. Talairach pitch differed from Schaltenbrand pitch by $5.81°\pm1.07°$. Talairach and Schaltenbrand pitch values had similar precision, with similar SDs ($10.2°$ and $10.4°$, respectively) and similar ranges ($48.3°$ and $48.3°$, respectively) (Table 1). Pitch variance ($104.2°$ Talairach and $107.5°$ Schaltenbrand) far exceeded that for roll ($13.5°$) or for yaw ($22.4°$) ($P<0.001$) (FIG. 7).

Figure 3:
FIG. 3 depicts measurements of canthomeatal angulation upon a surface-rendered brain, identifying orbital canthus and the external acoustic meatus.

Canthomeatal Pitch and Requisite Axial Coverage. Retrospective review of surface-rendered 3D datasets from the archetypical MNI brain (14) and averaged MNI brain (305 healthy volunteers) revealed that the canthomeatal pitch was approximately 9° steeper than the Talairach AC-PC line (FIG. 3). Given our mean pitch correction of $15.1°\pm10.2°$, axial oblique Talairach prescriptions better approximated standard CT canthomeatal angulation than routine axial imaging (9° vs. 24°) and Schaltenbrand angulation (9° vs. 15°).

The Talairach prescription also typically provides more efficient brain coverage than that of straight axial imaging. As illustrated in FIG. 4, the required coverage for the archetypical MNI brain (14) is approximately 8.1 mm less by using Talairach (134.2 mm) compared with straight axial prescription (142.3 mm). Similarly, analysis of the averaged MNI brain (15) and our archetypical clinical case in which the patient pitch was 15.1° relative to the Talairach line demonstrated a savings of approximately 8.0 and 5.3 mm, respectively.

Technologist Results. Technologist prescriptions for roll, yaw, and pitch are summarized in Tables 1 and 2 and in FIG. 7. As the clinical protocol required Talairach prescriptions, the technologists did not record Schaltenbrand observations. Thirteen technologists prescribed three or more studies (9.31-+-6.05). The Pearson correlation coefficient between roll-determination accuracy and the patient's absolute yaw was 0.48.

Computer Results. Prescriptions for roll, yaw, and pitch are summarized in Tables 1 and 2 and in FIG. 7. The Pearson correlation coefficient between the CATS roll determination accuracy and the patient's absolute yaw was 0.13.

In five cases, CATS could not identify the CC, and thus, it was unable to determine pitch. Because one of these cases also lacked a criterion standard, 120 of the original 126 cases were available for full comparison to the 124 cases with a criterion standard. Schaltenbrand measurements were not obtained with SPM'99, because the brain template used was Talairach and not Schaltenbrand as referenced.

All images were processed on a 2.0-GHz Pentium 4 PC (Dell, Tex.) running Windows 2000 Professional (Microsoft). Computer processing time for roll and yaw determination was less than 1 second per study. Pitch determination with our algorithm averaged 6.7 seconds±1.3 per study and approximately 20 seconds per study with the modified SPM'99 routine. A substantial portion of this performance difference resulted from the time needed to load the full 15 section dataset into memory for the SPM'99 method.

Comparison of Technologist and Computer Algorithms. Because of the presence of outliers, the paired t test may have been unreliable for our data. Instead, we chose to use the nonparametric sign or quantile test that is not heavily influenced by outliers or variations from a normal distribution (17). As can be seen in FIG. 7, technologist- and CATS-generated prescriptions substantially reduced inter-patient image variance with regard to roll, yaw, and pitch. TABLE 1: Prescribed angulation Discussion. The three-step Talairach prescription technique provides several potential advantages. The direct correction of roll and yaw facilitates inter-hemispheric comparison in the axial and coronal planes, respectively. Standardization of pitch further facilitates inter-subject comparison. The Talairach reference is an obvious choice, as it has already become the de facto standard for neurostereotaxis and functional imaging studies. Locating critical structures may be simplified. The Rolandic fissure, for example, consistently passes between the vertical (coronal) AC and PC planes. It originates caudally 0.5 cm in front or behind the vertical AC and terminates in the midline approximately 1-cm posterior to the vertical PC. Direct visual correlation with standard brain atlases or integration with existing software referenced to Talairach space may be facilitated without the need for reformatting. Such postprocessing may be time consuming and, unless isotropic 3D datasets are acquired, result in diminished in-plane resolution.

The Talairach reference line better approximates the canthomeatal line, which is routinely used for CT angulation, than either the Schaltenbrand line or the standard axial orientation. This improvement may facilitate the comparison of brain CT and MR images. Parenthetically, variation in patient's CT pitch prescriptions at our institution and at other centers is considerable. As such, it may be of benefit to study and standardize bony landmarks on lateral scout CT images that best approximate the canthomeatal or Talairach line. With CT, however, the radiation dose to the cornea and beam-hardening artifacts should also be considered.

Selecting the Talairach reference line allows for more efficient and consistent brain coverage than that typically obtained with conventional axial sectioning. The reduction of approximately 6 mm in requisite coverage translates to a savings of one or two images with our routine 4.0-mm sectioning. With the AC-PC protocol, most patients' brains are adequately imaged with 32 contiguous axial sections, resulting in a slight overall reduction in acquisition time on our MR imaging system.

Potential disadvantages do exist. On average, switching to the Talairach reference adds approximately 15°±10° of angulation to the axial plane of the magnet. This may add stress to the gradient system, and the triple oblique orientation may not be currently compatible with all pulse sequences. Additionally, the paranasal sinuses and nasopharynx may not be as fully imaged with the axial oblique sequences. Furthermore, protocol requires technologist training or automated software integration and additional, albeit short, setup and imaging time. Given the average requisite pitch correction, comparison to previously obtained straight (nonreferenced) brain MR imaging studies may be more difficult.

Without additional training, most MR imaging technologists can reliably and rapidly correct for roll and yaw, with remarkable accuracy with the latter. If desired, better accuracy for the former might be achieved if the technologists were to use an iterative approach to role determination when subsequent yaw correction exceeds a certain threshold. For example, if absolute raw correction exceeds 5° (as in 34 of 126 patients), a 2-second double oblique coronal localizer could be prescribed from the axial oblique localizer image to serve as a better template for subsequent sagittal prescription. Given a correlation coefficient of only 0.48, however, use of this additional sequence may not be justified for technologists outside the research setting. Moreover, with an even smaller correlation coefficient of 0.13, this iterative approach does not appear to have appreciable value for the computer algorithm.

Although several technologists performed well, the average technologist versus the criterion standard pitch discordance was significantly higher than the intra-author observer error (P<0.001). Technologist training beyond simply providing technique illustrations might improve pitch-correction accuracy. Practice datasets derived from our 126 case studies may be helpful.

Both the technologist- and computer-driven methods notably reduced inter-subject image variance in terms of roll, yaw, and pitch. However, because our study did not include infants or children, these results may not be generalized outside the adult population without further investigation. Nonetheless, as the CC, AC, and PC have attained a nearly adult configuration by 1 year of age, with minimal modification, we anticipate similar results beyond the first year and far better results than those achievable with single-template matching methods.

Although the CATS algorithm did not perform as well as the technologists in correcting yaw, the algorithm's mean absolute yaw error of only 1.46°±1.06° is believed to be within an acceptable range. CATS was more accurate than SPM'99 in correcting pitch, but it was unable to make a determination in four of 124 cases with criterion standard measurements. In such cases in which midline disease impaired delineation of the CC, the CATS algorithm could be extended to fall back to SPM'99-style template matching or to prompt for technologist prescription.

CATS may provide better precision than that of the technologists when roll, yaw, and pitch correction are determined on follow-up patient studies. In some applications, the algorithm advantageously automatically corrects for inter-image patient movement. Between imaging sequences, the 2-second FGRE coronal scout could be reacquired and compared with the original. If the computer detects inter-scan motion exceeding a certain threshold, the CATS algorithm could proceed with its 2-second FGRE axial oblique scout followed by a 2-second T2-weighted SSFSE midline double oblique localizer. Acquisition of an FGRE axial oblique scout image could be followed by a 2-second T2-weighted SSFSE midline double oblique localizer imaging (2). With a simple template-matching algorithm and the initially obtained midline sagittal T2 weighted FSE image constrained to translation and pitch rotation, inter-image patient motion could be automatically compensated for. This scheme could potentially permit accurate inter-image motion assessment in 3 seconds and automated tri-planar correction, if required, in an additional 6 seconds.

Our study was a proof of principle. As successful, we are currently attempting to implement our CATS and motion-compensation algorithms on several different MR imaging platforms. Interfacing with proprietary MR imaging systems, however, poses technical challenges unique to each vendor.

Direct integration of automated prescription algorithms into clinical MR imaging systems may reduce setup times and allow precise, operator-independent implementation of a wide range of brain imaging protocols referenced to Talairach space. For example, on the basis of the orientation of the hippocampus in the average MNI brain, we can prescribe oblique imaging perpendicular to the hippocampus by simply angling 56° steeper than the Talairach AC-PC line.

Conclusion. Whether automated or technologist driven, we advocate the use of direct Talairach-referenced brain MR imaging prescriptions as a new clinical standard and encourage manufacturers to facilitate their implementation. Direct roll-, yaw-, and pitch-corrected standardized brain MR images can be achieved by trained technologists or by automated computer algorithms to considerably reduce inter-patient image variance. The widely used Talairach AC-PC reference is recommended. Compared with straight axial imaging, this reference better approximates standard CT obliquity and provides more efficient brain coverage. Adoption of the Talairach AC-PC reference standard may lead to more reproducible and readily interpretable clinical brain MR images.

TABLE 1

Prescribed angulation

| Algorithm* | N | Mean | Median | Variance | SD | IQR | Minimum | Maximum | Range |
|---|---|---|---|---|---|---|---|---|---|
| Roll | | | | | | | | | |
| CS | 126 | −0.60 | −0.59 | 13.47 | 3.67 | 3.95 | −9.17 | 10.59 | 19.75 |
| Tech | 126 | 0.11 | 0.00 | 16.75 | 4.09 | 4.47 | −13.46 | 12.35 | 25.81 |
| CATS | 126 | −0.12 | −0.15 | 11.49 | 3.39 | 5.11 | −6.06 | 6.73 | 12.79 |
| Yaw | | | | | | | | | |
| CS | 126 | −0.86 | −0.94 | 22.38 | 4.73 | 6.20 | −11.17 | 17.26 | 28.43 |
| Tech | 126 | −0.26 | −0.32 | 20.02 | 4.47 | 6.00 | −9.48 | 18.51 | 28.00 |
| CATS | 126 | 0.01 | −0.61 | 18.80 | 4.34 | 6.78 | −8.49 | 16.21 | 24.70 |
| Talairach pitch | | | | | | | | | |
| CS | 124 | 15.16 | 15.11 | 104.23 | 10.21 | 12.97 | −8.13 | 40.20 | 48.34 |
| Tech | 126 | 15.59 | 15.25 | 99.59 | 9.98 | 14.28 | −18.78 | 38.85 | 57.64 |
| CATS | 121 | 13.86 | 14.04 | 111.03 | 10.54 | 14.66 | −10.39 | 41.42 | 51.81 |
| SPM'99 | 126 | 11.95 | 10.96 | 6056 | 7.78 | 10.80 | −4.40 | 30.04 | 40.45 |
| Schaltenbrand pitch | | | | | | | | | |
| CS | 124 | 9.35 | 8.63 | 107.62 | 10.37 | 13.60 | −14.62 | 33.69 | 48.31 |
| CATS | 121 | 9.97 | 9.02 | 115.37 | 10.74 | 14.36 | −13.82 | 38.97 | 52.78 |

*CS indicates criterion standard; Tech, technologist; IQR, inter-quartile range.

TABLE 2

2 Deviation from the criterion standard

| Algorithm* | N | Mean | Median | Variance | SD | IQR | Minimum | Maximum | Range |
|---|---|---|---|---|---|---|---|---|---|
| Roll | | | | | | | | | |
| PA | 126 | 0.60 | 0.59 | 13.47 | 3.67 | 3.95 | −10.59 | 9.17 | 19.75 |
| Tech | 126 | 0.71 | 0.78 | 3.42 | 1.85 | 1.99 | −4.29 | 6.81 | 11.1 |
| CATS | 126 | 0.48 | 0.66 | 3.92 | 1.98 | 1.63 | −8.21 | 9.37 | 17.6 |
| Yaw | | | | | | | | | |
| PA | 126 | 0.86 | 0.94 | 22.38 | 4.73 | 6.20 | −17.26 | 11.17 | 28.43 |
| Tech | 126 | 0.59 | 0.63 | 0.65 | 0.81 | 0.97 | −2.50 | 2.57 | 5.1 |
| CATS | 126 | 0.86 | 196 | 2.52 | 1.59 | 2.11 | −2.40 | 4.73 | 7.1 |
| Talairach pitch | | | | | | | | | |
| PA | 124 | −15.16 | −15.11 | 104.23 | 10.21 | 12.97 | −40.20 | 8.13 | 48.34 |
| Tech | 124 | 0.56 | 1.15 | 28.62 | 5.35 | 2.88 | −24.62 | 20.68 | 45.3 |
| CATS | 120 | −1.23 | −1.11 | 18.52 | 4.30 | 3.60 | −23.41 | 14.81 | 38.2 |
| SPM'99 | 124 | −3.14 | −1.56 | 59.30 | 7.70 | 5.23 | −37.96 | 9.88 | 47.8 |
| Schaltenbrand pitch | | | | | | | | | |
| PA | 124 | −9.35 | −8.63 | 107.62 | 10.37 | 13.60 | −33.69 | 14.62 | 48.31 |
| CATS | 120 | 0.70 | 1.13 | 18.30 | 4.28 | 4.07 | −20.41 | 15.48 | 35.9 |

*PA indicates physical alignment; Tech, technologist; IQR, inter-quartile range.

CT Brain Prescriptions in Talairach Space: A New Clinical Standard.

BACKGROUND AND PURPOSE: Head CT prescriptions are currently plagued by intra- and inter-subject image variance and do not match standardized MR imaging planes. We developed and tested a simple method to improve CT precision and approximate the Talairach reference standard advocated for MR imaging.

METHODS: We retrospectively reviewed midline sagittal T2-weighted brain MR images of 126 consecutive patients to determine the mean angle subtended by the Talairach anterior commissure-posterior commissure (AC-PC) line and the hard palate. On the basis of this data set, a new head CT protocol was instituted with pitch similarly prescribed relative to the hard palate as identified on the lateral CT scout film. We then compared the precision of the new protocol, our former method (nominally parallel to the orbito-meatal line) and fixed-gantry angulation. Two head CT studies from 50 consecutive patients imaged with our old protocol and 50 consecutive patients imaged with our new protocol were reviewed for a total of 200 CT examinations.

RESULTS: The Talairach AC-PC line was rotated 12.0°±6.1° from the hard palate line and 15.6°±10.1° from the axial plane of the magnet. The new CT protocol approximated the Talairach-referenced MR images obtained at our institution and improved intra-patient CT scan precision compared with fixed-gantry selection (P<0.004) and compared with our previous prescription technique (P<0.064; P<0.025, controlling for excessive head extension).

CONCLUSION: By prescribing CT images angled +12° from the hard palate, a structure readily identified by technologists, inter-scan precision can be improved and Talairach-referenced MR imaging studies can be approximated. Along with AC-PC-referenced MR imaging studies, we advocate this CT protocol as a new clinical standard.

Variability in head positioning and prescribed techniques for MR imaging and CT may yield significant intra- and inter-subject image variance within and across modalities. Having already become a de facto standard for neuroscience research and stereotaxis, the Talairach reference has been recently advocated as a new standard for clinical brain MR imaging. Recently, both technologist- and computer-driven methods to directly prescribe Talairach-referenced MR images have demonstrated a substantial reduction in inter-patient scan variance and more efficient brain coverage than routine clinical axial imaging.

CT head scans have been traditionally prescribed parallel to the orbito-meatal line (OML), defined as passing through the lateral canthus and middle of the external ear canal. Use of this external reference line for CT prescriptions, however, has several major drawbacks. First, it is difficult to discern the OML on the lateral scout view from which technologists currently prescribe. Second, if a patient's head is extended, scanner limitations in gantry angulation (e.g., 22° for most GE CT scanners [General Electric Corporation, Milwaukee, Wis.]) may preclude accurate OML prescription. These two factors can lead to significant prescription errors and inter- and intra-subject CT image variance. In addition, the OML may have a relatively inconstant relationship to superficial and deep brain structures, resulting in further inter-subject variance in the appearance of the brain on axial CT sections. Finally, the OML matches neither conventional MR axial sectioning nor Talairach anterior commissure-posterior commissure (AC-PC)-referenced imaging, being approximately 24° steeper than the former and 9° steeper than the latter. As a result, axial head CT scans parallel to the OML may be difficult to directly compare with axial brain MR imaging sections, particularly those conventionally prescribed orthogonal to the bore of the magnet.

We developed and tested a simple method to improve CT precision and approximate the Talairach reference standard advocated for MR imaging by using the hard palate as a landmark. The hard palate was selected because it is a relatively planar midline structure fixed to the skull and projects as a line on the lateral CT scout film. In addition, this readily identifiable landmark is already used by technologists to prescribe maxillofacial CTs.

Figure 8:
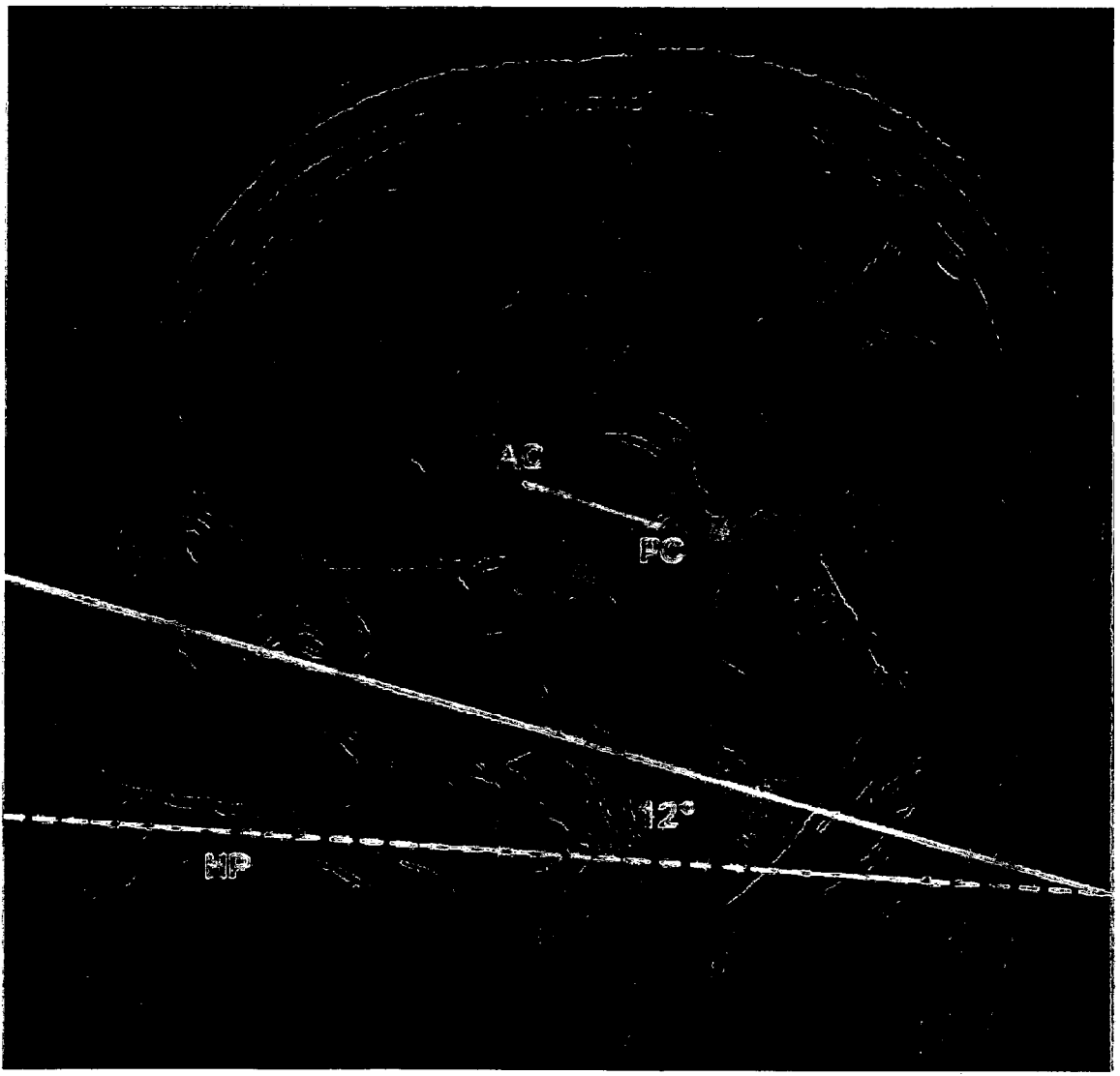
FIG. 8 is a midsagittal, T2-weighted clinical brain MR image annotated with a mean angle subtended by the Talairach AC-PC line and the hard palate.
Figure 9:
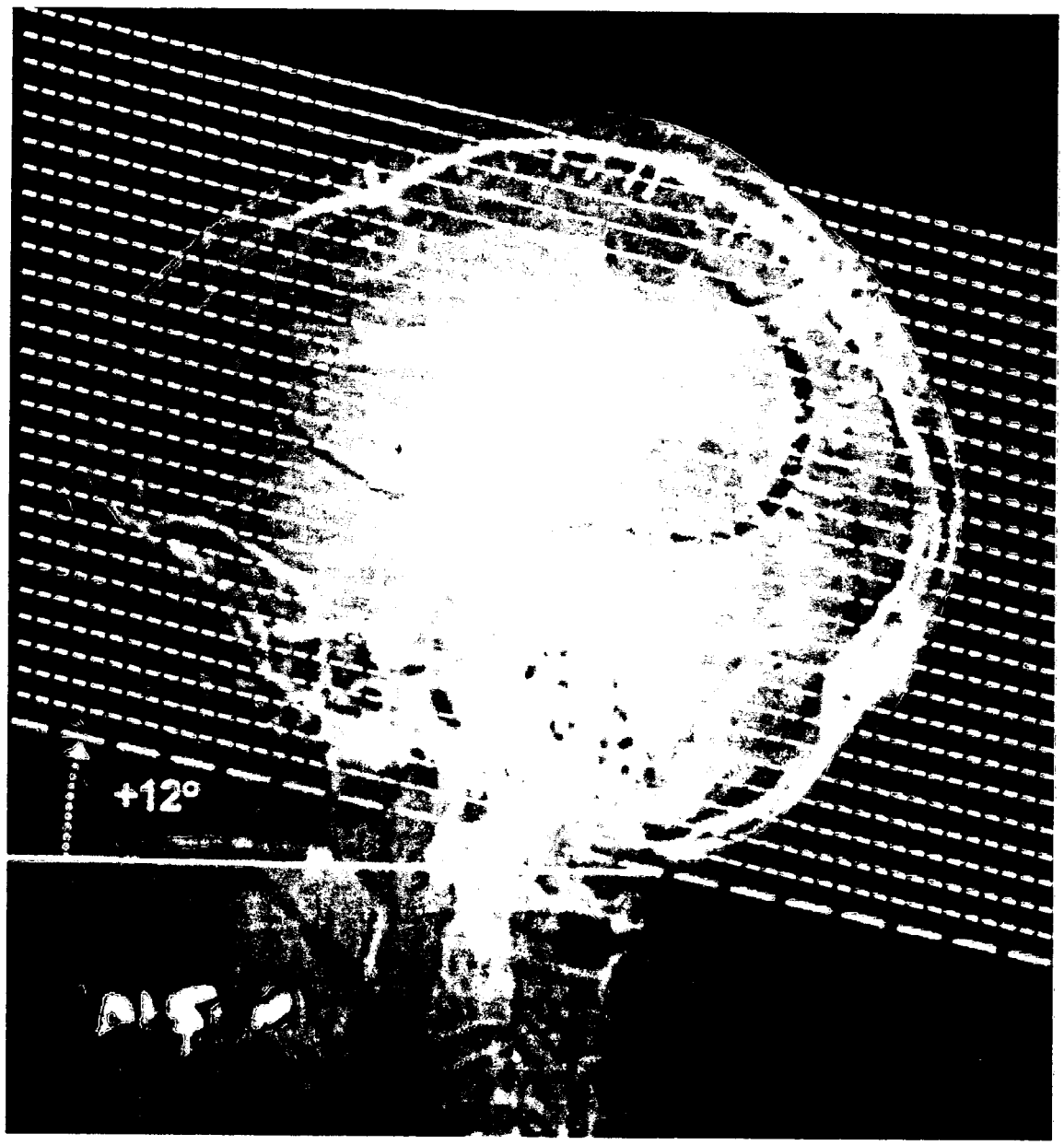
FIG. 9 is a lateral CT scout view from a study patient illustrating the axial scan prescription (dotted lines) angled 12 degrees from a line passing through the hard palate (solid line). The solid line indicating the orientation of the hard palate has been offset a few millimeters inferiorly to provide a clear view of the hard palate.
Figure 10A:
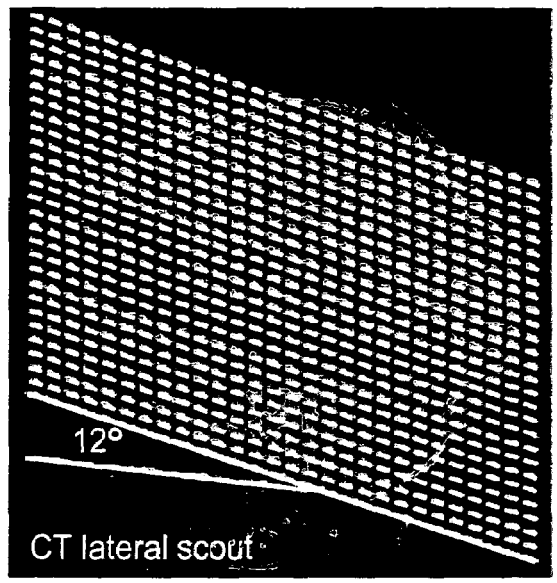
FIG. 10A-I are consecutive CT and MR examinations from the same subject taken on different days, with FIGS. 10A-C illustrating axial CT and MR image prescription, FIGS. 10D-F and FIGS. 10G-I respectively illustrative representative axial sections from these examinations through the orbits and posterior fossa with differing CT windows or MR sequencing.
Figure 10B:
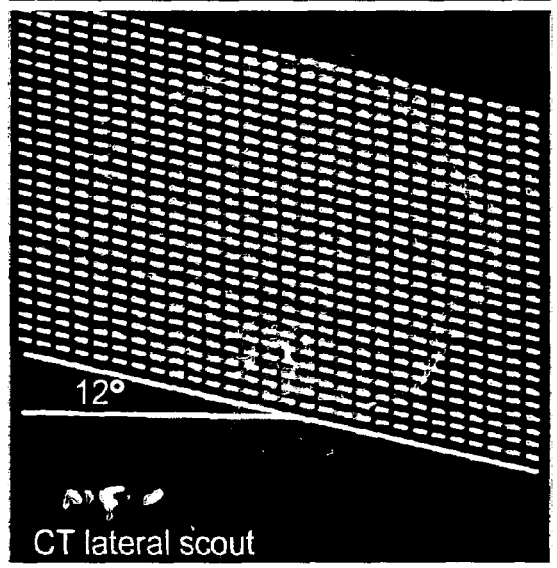
Figure 10C:
Figure 10D:
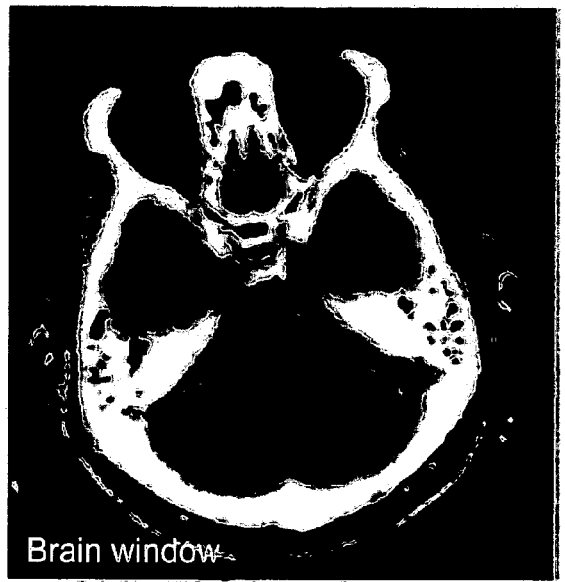
Figure 10E:
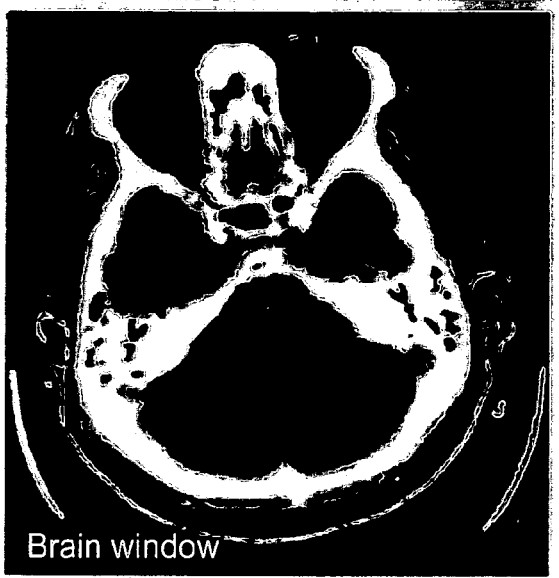
Figure 10F:
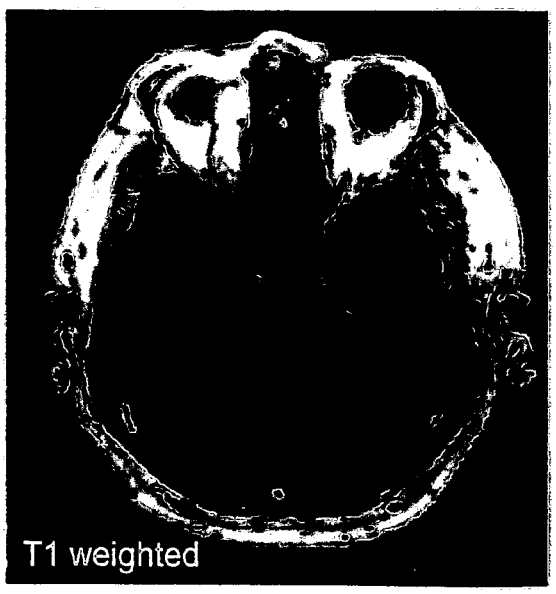
Figure 10G:
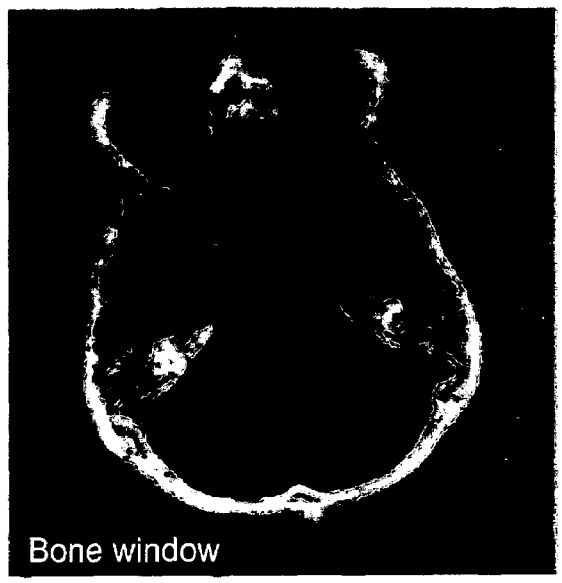
Figure 10H:
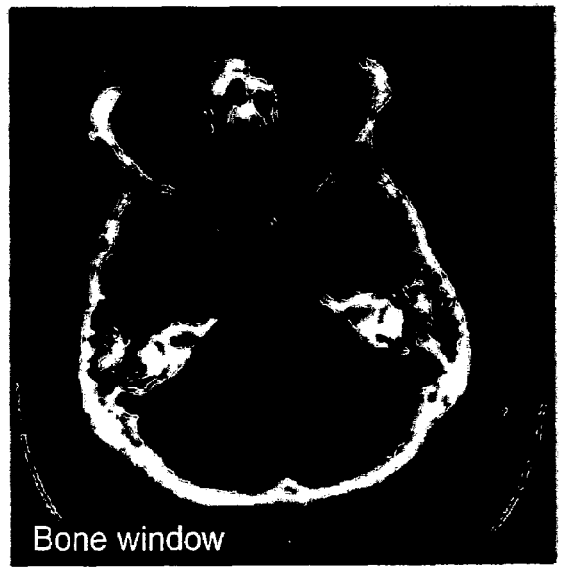
Figure 10I:
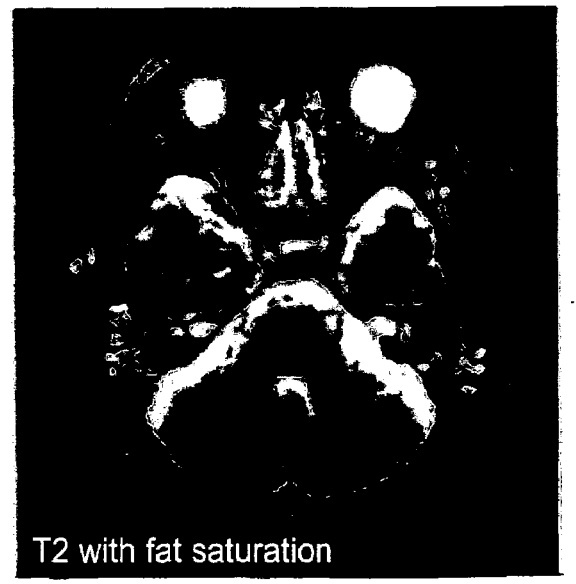

Methods. Institutional review board approval was obtained. Subsequently, to determine the mean angle subtended by the Talairach AC-PC line and the hard palate, two co-authors (K L. W. and J. S.) retrospectively reviewed a data base of 126 midsagittal, T2-weighted clinical brain MR images produced from May 7, 2002 to May 21, 2002 at our institution. (FIG. 8) The MR imaging population consisted of 64 male and 62 female subjects ranging in age from 17 to 89 years, with an average age (+SD) of 49.2 (±17.8). On Nov. 15, 2002, we instituted a new clinical head CT protocol (HP+12) in which scan pitch (i.e., gantry tilt) was to be offset by this predetermined angle relative to the hard palate as identified by technologists on the lateral CT scout film (FIG. 9). This protocol replaced our former protocol (OML*) in which the technologists were instructed to angle the gantry parallel to the OML as visualized on the lateral scout, albeit difficult to identify. The asterisk designates the technologist approximation of the OML from the lateral scout rather than the true anatomic OML.

To compare the performance of our new protocol (HP+12) against our former protocol (OML*) and an alternate hypothetical fixed-gantry protocol (AX+15) optimized to approximate the Talairach AC-PC line, we reviewed a total of 200 head CT examinations. These included 50 consecutive patients with two head CT studies taken by usng the OML* protocol and 50 consecutive patients with two head CT studies taken with the HP+12 protocol. The CT scan population consisted of 56 male and 44 female subjects. Patient age was only available for 57 of the patients and ranged from 16 to 93 years, with a mean of 49.8 years (±17.6).

For each CT study, the lateral CT scout and technologist selected gantry angle for axial sections were collected for review, the latter obtained from the DICOM header. Hard palate angles relative to the horizontal plane were measured independently on all 200 CT scouts by three co-authors (K. L. W., J. L. W., and W. S.) and were subsequently reviewed together by the same three co-authors en banc to establish a hard-palate angle consensus and determine a gantry detector tilt co-author-derived criterion standard. For the alternate fixed-gantry protocol, the average hard palate angle was used. The sign convention for angle measurements defines head extension as positive.

Pearson correlation coefficients were compared for the OML* and HP+12 protocols. Precision and accuracy relative to the co-author criterion standard for each gantry tilt method was also evaluated. The accuracy of a particular study was measured as the absolute difference between the technologists elected gantry angle and the co-author criterion standard:

$$E_{accuracy} = |\theta_{CT\ gantry} - \theta_{CT\ standard}| \tag{1}$$

The precision or reproducibility of each method was calculated as the absolute difference in prescription accuracy for each pair of CT scouts obtained from the same subject:

$$E_{precision} = |(\theta_{CT1\ gantry} - \theta_{CT1\ standard}) - (\theta_{CT2\ gantry} - \theta_{CT2\ standard})| \tag{2}$$

To adjust for population bias and isolate the influence of our CT scanner's 22° maximum gantry tilt limitation, full and reduced data sets for the OML* and HP+12 technologist method protocols were compared. The reduced data set consisted of only those scans requiring a gantry tilt less than or equal to 22° as determined by the co-author-derived hard-palate criterion standard.

Statistical analysis was performed by using DSTPLAN, NCSS 2001, and Microsoft Excel. A statistical significance threshold of a =0.05 was applied for all inferences.

Results. Paired measurements of the Talairach AC-PC reference and hard palate could be obtained for only 117 of the 126 MR imaging studies because of distorted anatomy, artifact, or limited field of view. For these 117 studies, the Talairach AC-PC line was extended by 12.0° (±6.1°) from the hard palate line and 15.6° (±10.1°) from the axial plane of the magnet. Consequently, to approximate the Talairach AC-PC line protocol, the HP+12 CT protocol prescribes CT gantry detector tilt at +12° extension from the hard palate as identified by the technologists on lateral CT scout film.

Average technician-prescribed gantry tilt by using the OML* protocol was 11.1° (±8.6°) and 13.4° (±7.5°) by using the HP+12 protocol. In all 200 CT lateral scout images, a co-author consensus for the hard palate orientation was achieved. inter-author correlation coefficients for hard palate angle measurements from the CT lateral scout ranged from 0.90 to 0.95, and individual author correlation with the hard palate criterion standard ranged from 0.94 to 0.98. The hard palate in all lateral scout CTs studied was extended an average 3.0° (±11.9°).

Overall, the standard hard palate extension averaged 3.0° (±11.9°). For the alternate hypothetical fixed-gantry protocol (AX+15), we chose a fixed-gantry tilt of 15° to best approximate the Talairach AC-PC line as extended +12° from the overall average hard palate angulation of 3.0° on lateral scout CT to arrive at a hypothetical fixed-gantry tilt of 15°.

The patient heads studied with the HP+12 protocol were more extended than those studied with the OML* protocol. This introduced a significant population bias, in view of the 22° maximum gantry tilt permitted on our GE scanners. To compensate for this bias, a reduced data set was created by selecting only CT scans that require gantry prescriptions no greater than 22°. The reduced data set excludes 56 (25 OML* scans and 31 HP+12 scans) of the 200.

The difference in correlation of the OML* (R=0.78) and HP+12 (R=0.82) prescriptions with the co-author criterion standard was not statistically significant when comparing full data sets (P=0.18; power=0.23; Table 3A). The HP+12 method, however, was more strongly correlated with the criterion standard (R=0.87) than was the OML* method (R=0.69) for the reduced data set (P<0.003; power=0.87; Table 3B). Correlation analysis does not apply to the AX+15 fixed-gantry protocol because a constant prescription of 15° was used.

Due to the use of absolute values, the distributions of accuracy and precision metrics were significantly nongaussian. To derive inferential statistics, data transformations were tested. Cubic-root transformation was found to significantly improve the normalcy of all variables and was subsequently applied.

Both the HP+12 and OML* technologist protocols were more accurate than the fixed-gantry AX+15 alternative (P<0.0001). There was no statistical difference between the accuracies of the HP+12 and OML* protocols for the full data set (P=0.71; power=0.07; Table 3A) For the reduced data set, however, the accuracy of the HP+12 protocol was superior to that of the OML* protocol (P=0.004; power=0.83; Table 3B).

The HP+12 protocol was more precise than the fixed-gantry alternative AX+15 protocol (P=0.004; power=0.85). The OML* protocol did not significantly improve precision relative to the fixed-gantry AX+15 protocol (P=0.18; power=0.24). There was also evidence of improved precision by using the HP+12 protocol relative to the OML* protocol, but this did not demonstrate statistical significance at a =0.05 for the full data set (P=0.06; power=0.46; Table 3A). For the reduced data set, the precision of the HP+12 protocol was superior to that of the OML* protocol (P=0.025; power=0.63; Table 3B).

Discussion. Institution of the aforementioned CT prescription protocol was easy for our technologists and did not require special training. Concurrently, we changed our routine section thickness from 5 mm through the posterior fossa and 10 mm above to contiguous 5-mm-thick sections through the entire brain. This simplifies brain prescriptions, improves inter-scan image concordance by reducing maximum offset from 5 to 2.5 mm, permits subsequent whole brain multiplanar reconstructions on our multidetector scanners, and better approximates our routine 4-mm MR imaging brain sectioning. In addition, we reduced our field of view from 25 to 22 cm to increase in-plane spatial resolution and better approximate our MR imaging studies typically performed with a 20-cm field of view.

Although readily identifiable on lateral CT scout films, the hard palate may have some limitations as a landmark for pitch determination. The superior surface of the hard palate appears grossly planar, but curvature may exist. Coupled with the relatively short anteroposterior dimension of the hard palate, this curvature could yield some inherent inter-observer error. Nonetheless, as hypothesized, using the hard palate as a landmark did improve CT scan precision and accuracy relative to fixed-gantry angulation and to the OML* and AX+15 protocols, the latter nominally relying on the OML. Unexpectedly, the technologist-selected OML* was less extended than the HP+12 line designed to approximate the Talairach AC-PC reference. Two factors could be contributory, either our technologists were choosing landmarks offset from the patient's actual OML or the patient population did not approximate the 305 healthy volunteer Montreal Neurological Institute (MNI) brain population in this measurement. In light of the difficulty of discerning the OML on lateral CT scout films, we believe the former factor likely predominates, hence the asterisk in the OML* designation.

By approximating the Talairach AC-PC line in an individual patient, the HP+12° protocol may be discordant with the Talairach reference, reducing CT-MR imaging inter-modality precision. In our study, the angle subtended by the hard palate and the AC-PC line varied from patient to patient (SD=6.3°). Consequently, excellent CT-MR imaging concordance, as demonstrated in FIG. 10, would be expected to occur only when an individual's subtended angle closely approximates the mean of 12°. (FIGS. 8 and 10)

To improve inter-modality image concordance, implementing the HP+12° CT algorithm should ideally be done in conjunction with adoption of the Talairach MR imaging reference standard. If for technical, anatomic, or pathologic reasons technologists can identify the hard palate but not the AC and PC on a patient's midline sagittal MR imaging, the MR imaging study could be prescribed in a similar fashion to that suggested for brain CT scans; that is, 12° steeper than the hard palate. Theoretically, this should further reduce CT-MR imaging inter-modality variance while approximating the desired Talairach AC-PC pitch.

Figure 11:
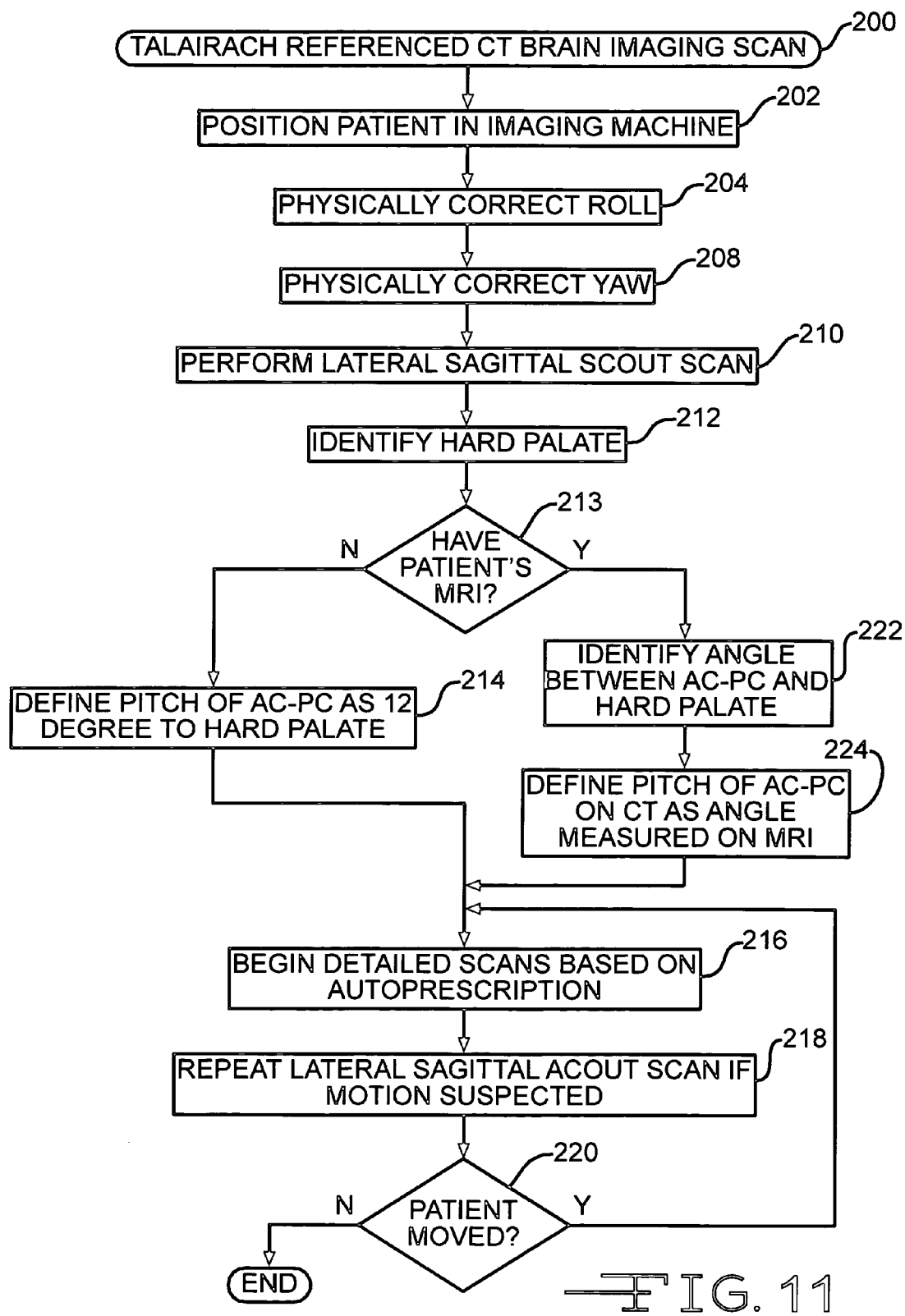
FIG. 11 depicts a flow diagram or sequence of operations for performing pitch correction during a pre-scan based upon locating the hard palate, and also illustrates periodic reaccomplishment of the roll, yaw, pitch correction to adjust for inadvertent patient repositioning.

In contradistinction to the three-step protocol proposed by Weiss and co-authors for providing direct Talairach-referenced MR imaging examinations, the CT protocol may not necessarily compensate for patient roll and yaw. Consequently, in reference to a procedure for tri-planar brain imaging scan 200 in FIG. 11 to optimize CT results, care should be given to ensure that the patient's head is not significantly rotated within the head holder/gantry (block 202). Moreover, when using a CT scanner constrained by a maximum gantry tilt of less than 30°, significant head extension should be avoided as much as possible. Unfortunately, in the acute trauma setting, technologists may not be able to readily or safely reposition the patient's head. Thus, head roll should be corrected (block 204) and head yaw should be corrected (block 208). A lateral sagittal scout scan is performed (block 210). In instances where the CC is visible, identifying the Talairach AC-PC reference line may be accomplished as previously discussed. If not, image analysis may be performed to identify the hard palate (block 212). If an MRI image from the same patient with known Talairach AC-PC reference line, then head pitch of the AC-PC reference line of 12 degrees from the hard palate may be defined (block 214). Having thus oriented from the prescan, prescriptions for detailed scans may be performed (block 216). Since some detailed scans may require a number of minutes, advantageously all or part of a three-step process for roll, yaw and pitch correction may be repeated (block 218). If this orientation check indicates that the patient has moved, then portions of the detailed scans may be repeated by returning to block 216 and/or the new orientation correction may be used for subsequent detailed scans to reduce intra-patient variation.

Alternatively, if an MRI image was determined to be available in block 213, then the angle between the AC-PC reference line and hard palate my be measured (block 222). The pitch of the AC-PC on the CT image is thus defined as the identified angle measured on the MRI image (block 224) and processing continues to block 216.

In view of the study's urban trauma level-one medical center setting and the two-CT-examination inclusion criteria, our scan population was strongly biased to acute traumatic injury. Consequently, higher precision might be expected in a different setting, such as an outpatient imaging facility or with CT scanners that permit greater gantry angles. Because our study did not include infants or children, the results may not yet be generalized outside the adult population. Further investigation is currently under way to include evaluation of the proposed methodology in pediatric patients.

Conclusion. By prescribing CT images angled 12° from the hard palate, inter-scan precision can be improved and Tailarach-referenced MR imaging studies can be approximated. Along with Talairach AC-PC-referenced MR imaging studies, we advocate this CT protocol as a new clinical standard. Adoption of these complementary CT and MR imaging prescription protocols should facilitate intra- and inter-modality comparisons, leading to more reproducible and readily inter-pretable brain imaging findings.

TABLE 3

Comparative performance of prescription protocols

| Protocol | R | Accuracy | | | Precision | | |
|---|---|---|---|---|---|---|---|
| | | Mean | SD | N | Mean | SD | N |
| A. Full Data Set[a] | | | | | | | |
| AX + 15 | | 9.36° | 7.38° | 200 | 7.53° | 5.11° | 100 |
| OML* | 0.78 | 5.73°[c] | 4.56° | 100 | 6.67° | 5.34° | 50 |
| HP + 12 | 0.82 | 5.98°[c] | 5.73° | 100 | 5.32°[c] | 4.38° | 50 |
| B. Reduced Data[d] | | | | | | | |
| AX + 15 | | 7.18° | 6.78° | 147 | 7.34° | 5.38° | 66 |
| OML* | 0.69 | 4.87°[c] | 3.99° | 78 | 6.77° | 5.97° | 35 |
| HP + 12 | 0.87[d] | 3.27°[c,d] | 2.87° | 69 | 4.37°[c,d] | 3.79° | 31 |

[a]Results for the full data set.
[b]Results controlled for head extension requiring gantry tilt prescription greater than 22°.
[c]Significant improvement (P < 0.05) versus AX + 15 protocol.
[d]Significant improvement (P < 0.05) versus OML* protocol.

Iterative Scan Presciptions for Optimized Magnetic Resonance Imaging (MRI) of the Neuro-Axis.

The afore-described algorithms and an associated three-step clinical protocol rapidly, accurately, and reproducibly prescribe the imaging planes of brain MRIs. A series of scout images allows the anterior and posterior commissure landmarks that form the basis of the Talairach reference to be identified. These landmarks are currently used to prescribe standardized axial planes.

Rather than the generally known approach of using MRI scan planes and sequences that are currently prescribed by technologists, computer algorithms automate each step of the clinical protocol. As an extension thereof, it should be appreciated that these algorithms may be fully integrated and optimized for real-time use on both clinical and investigational MRI scanners. Integration directly in the imaging pipeline allows extensions of these algorithms to assess and compensate for patient motion between scans, ensuring optimally co-registered MR sequencing within and across studies, all prospectively registered in Talairach space. By directly integrating MR scanners with algorithms that provide a reproducible and standardized anatomical space (e.g., Talairach space), an advanced platform for new anatomy-aware protocols may be created.

Because the algorithms in some applications may not be used in real-time, current use of the Talairach landmarks is limited to prescription of planes closely associated with the Talairach reference plane and manually selected by technologists, such as oblique axial MR parallel to the Talairach plane. Integration into scanner software may enable advanced protocols that include knowledge of brain anatomy as well as real-time adaptive "expert" scan protocols. Brain atlases may be used in real-time for prescription and these prescriptions will be entered in atlas coordinates. Expert systems will be developed and optimized using more complex anatomy-aware protocols involving iterative loops of real-time computer-aided detection of brain pathology to include stroke and aneurysms and brain protocols tailored specifically to the patient while within the magnet.

Talairach referenced axial diffusion-weighted images (DWI), whether prescribed by a technologist or a computer, are currently obtained following the initial roll and yaw corrected sagittal T2 sequence. If computer image analysis of the initial DWI sequence suggests regions of acute infarction, the basic brain protocol may be streamlined and modified to include MR angiography and perfusion sequencing. This would respectively permit evaluation of the underlying vascular lesion and the detection of potential perfusion/diffusion mismatches directing emergent neuro-vascular intervention. Stroke is the leading cause of disability in this country. Because the time to emergent therapy strongly inversely correlates with morbidity and mortality, the development and implementation of the proposed computer algorithms could significantly improve patient outcome.

An example application is using MR angiography for patients at risk for intra-cranial aneurysms. Co-registered white and black blood MR angiography sequences uniquely facilitates computer-aided diagnosis and analysis of potential aneurysms in this population. If computer image analysis of such initial MRA screening sequences reveals a potential aneurysm, dedicated phase-contrast images of the putative aneurysm may be iteratively prescribed to better characterize the lesion and assess flow characteristics. Computer flow modeling and other engineering analysis may provide a better stratification of an individual aneurysm's risk for rupture, leading to more optimized patient management as the majority of brain aneurysms do not rupture and therapeutic intervention (coiling or clipping) carries morbidity and mortality risks. Tobacco smoking significantly increases the incidence ischemic brain disease as well as aneurysms and their rupture leading to catastrophic stroke.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while MRI and CT diagnostic imaging have been discussed in detail, it should be appreciated that applications consistent with the present invention may include other types of diagnostic imaging.

For another example, while Cartesian coordinates described relative to the patient (i.e., roll, yaw, pitch) have been described herein, it should be appreciated that other coordinate systems may be employed to prescribe detailed scans, depending upon the scanning equipment conventions (e.g., cylindrical coordinates, spherical coordinates).

What is claimed is:

1. A method of identifying a head position of a patient undergoing diagnostic imaging, comprising:

obtaining a diagnostic image of a patient's head with a diagnostic imaging machine;

performing an automated image processing operation to determine coordinates of a Talairach anterior commissure (AC)—posterior commissure (PC) reference line within the diagnostic image by identifying a line passing through a hard palate on the diagnostic image and utilizing the identified line to approximate the Talairach AC-PC reference line as about 12 degrees more extended than the hard palate in a lateral midline image; and defining a coordinate system of the diagnostic image with reference to the Talairach AC-PC reference line.

2. The method of claim 1, further comprising:

prescribing a subsequent scan based on the identified Talairach AC-PC reference line and coordinate system; and repeating the automated image processing operation to determine current coordinates of the Talairach AC-PC reference for accommodating changes in patient head position since the previous position determination.

3. The method of claim 1, wherein obtaining a diagnostic image comprises obtaining a roll and yaw corrected thin section midsagittal magnetic resonance imaging (MRI) image of the patient's head.

4. The method of claim 3, wherein obtaining a midsagittal MRI image of a patient's head further comprises:

obtaining at least two scout views;

identifying midline features to permit correction of roll and yaw; and obtaining a midsagittal MRJ image based on identified midline features.

5. The method of claim 4, wherein obtaining a midsagittal MRI image of a patient's head when identifying midline features to permit correction of roll and yaw further comprises:

performing at least one rapid scan operatively configured to accentuate venous blood flow in the superior sagittal sinus (SSS) in a plane selected from a group consisting of coronal scan, axial scan and oblique scan of the patient's head;

identifying the SSS in cross-section in the at least one rapid scan;

identifying a line that bisects the brain with the line passing through the SSS cross-section; and defining an attitude correction selected from a group consisting of roll correction and yaw correction corresponding to the selected plane for subsequent scans based on the identified line that bisects the brain.

6. The method of claim 1, wherein obtaining a diagnostic image comprises obtaining a lateral computerized tomography (CT) scout image.

7. The method of claim 6, wherein obtaining a lateral CT scout image of a patient's head further comprises physically adjusting patient's head position relative to a scanner that obtains the lateral CT scout image for minimizing roll and yaw visually.

8. A program product embodied in a tangible, recordable media, comprising:

(a) a program configured to receive a thin section diagnostic image of a patient's brain from a CT diagnostic imaging machine and to determine coordinates of a Talairach anterior commissure (AC)— posterior commissure (PC) reference line within the thin section diagnostic image and to define a coordinate system of the diagnostic image with reference to the Talairach AC-PC reference line; and (b) a tangible signal bearing media bearing the program; wherein the diagnostic image is a lateral computerized tomography (CT) scout image, wherein the program is further configured to receive a midline sagittal MR scan from an MR diagnostic imaging machine, and wherein the program is further configured to:

(a) identify a line passing through the hard palate on the MR scan;

(b) calculate an angle between the patient's hard palate and the Talairach AC-PC reference line in the MR scan;

(c) identify a line passing through the patient's hard palate on the diagnostic image; and, (d) utilize the calculated angle to adjust a CT pitch prescription.

9. The program product of claim 8, wherein determining coordinates of the Talairach AC-PC reference line comprises iteratively searching for and identifying landmarks on the diagnostic image, these landmarks selected from the group consisting of superior sagittal sinus (SSS), corpus callosum, a rostrum of the corpus callosum, an inferior edge splenium of the corpus callosum, mammilary bodies, fornices, and a superior margin of a brainstem.

10. The program product of claim 8, wherein the diagnostic image is a roll and yaw corrected sagittal image section, and wherein wherein determining coordinates of the Talairach AC-PC reference line comprises:

a) referencing a template dataset with a known Talairach AC-PC reference line; and b) iteratively minimizing a difference between the sagittal image section and the template dataset.

11. The program product of claim 10, wherein referencing the template dataset further comprises obtaining a previous scan of the same patient with a known Talairach AC-PC reference line.

12. The program product of claim 10, wherein referencing the template dataset further comprises obtaining an institutional standard dataset of an averaged template with a known Talairach AC-PC reference line.

* * * * *

UNITED STATES PATENT AND TRADEMARK OFFICE
CERTIFICATE OF CORRECTION

PATENT NO. : 7,450,983 B2
APPLICATION NO. : 10/803700
DATED : November 11, 2008
INVENTOR(S) : Kenneth L. Weiss It is certified that error appears in the above-identified patent and that said Letters Patent is hereby corrected as shown below:

In the paragraph beginning on line 42 of column 2, the following changes should be made:

FIGS. 5A-5C are an illustration of computer automated three-step functionality. FIG. 5A is an image of APE to determine the positions of the scalp and CC by examining intensities along the central column of pixels from a midline sagittal T2-weighted image. FIG. 5B is an image of automated contours and a bisecting line on a 2-second axial oblique T1-weighted gradient-recalled echo image. FIG. 5C is an image of an outline of the CC, triangle search mask, and Talairach AC-PC reference line on a midline sagittal T2-weighted image.

In the paragraph beginning on line 65 of column 13, the following changes should be made:

To compare the performance of our new protocol (HP +12) against our former protocol (OML*) and an alternate hypothetical fixed-gantry protocol (AX+15) optimized to approximate the Talairach AC-PC line, we reviewed a total of 200 head CT examinations. These included 50 consecutive patients with two head CT studies taken by using the OML* protocol and 50 consecutive patients with two head CT studies taken with the HP+ 12 protocol. The CT scan population consisted of 56 male and 44 female subjects. Patient age was only available for 57 of the patients and ranged from 16 to 93 years, with a mean of 49.8 years (± 17.6).

Signed and Sealed this

Thirteenth Day of January, 2009

JON W. DUDAS
*Director of the United States Patent and Trademark Office*